United States Patent
Mamedov et al.

(10) Patent No.: US 8,013,196 B2
(45) Date of Patent: Sep. 6, 2011

(54) PROCESS FOR THE PRODUCTION OF ETHYLENE

(75) Inventors: Aggadin Mamedov, Houston, TX (US); Saeed Al-Wahabi, Riyadh (SA); Yungyi Lin, Riyadh (SA); Mohamed Sabri Abdelghani, Riyadh (SA); Akram Al-Alwan, Riyadh (SA)

(73) Assignee: Saudi Basic Industries Corporation, Ryadh (SA)

( * ) Notice: Subject to any disclaimer, the term of this patent is extended or adjusted under 35 U.S.C. 154(b) by 308 days.

(21) Appl. No.: 11/988,349

(22) PCT Filed: Jun. 22, 2006

(86) PCT No.: PCT/EP2006/006225
§ 371 (c)(1),
(2), (4) Date: Jan. 12, 2009

(87) PCT Pub. No.: WO2007/003312
PCT Pub. Date: Jan. 11, 2007

(65) Prior Publication Data
US 2009/0198090 A1    Aug. 6, 2009

(30) Foreign Application Priority Data
Jul. 6, 2005 (EP) .................................. 05014585

(51) Int. Cl.
*C07C 5/09* (2006.01)
(52) U.S. Cl. ........ 585/257; 585/250; 585/254; 585/310; 585/324; 585/500; 585/648; 585/650; 585/652; 585/654; 585/656; 585/659
(58) Field of Classification Search ............. 585/310, 585/324, 257, 250, 254, 500, 648, 650, 652, 585/654, 656, 659
See application file for complete search history.

(56) References Cited

U.S. PATENT DOCUMENTS

| | | | |
|---|---|---|---|
| 3,267,170 A | 8/1966 | Aldridge at at. | |
| 3,321,545 A | 5/1967 | Rigney et al. | |
| 4,128,595 A | 12/1978 | Montgomery | |
| 4,520,224 A * | 5/1985 | Kamimura et al. | 585/648 |
| 4,726,913 A | 2/1988 | Brophy et al. | |

(Continued)

FOREIGN PATENT DOCUMENTS
GB        921305        3/1963
(Continued)

OTHER PUBLICATIONS
Sundaram, "Ethylene" in Kirk-Other Encyclopedia of Chemical Technology, J. Wiley and Sons, available on-line Apr. 16, 2001.*
(Continued)

*Primary Examiner* — In Suk Bullock
*Assistant Examiner* — Bradley Etherton
(74) *Attorney, Agent, or Firm* — Cantor Colburn LLP

(57) ABSTRACT

The invention relates to a process for the production of ethylene, comprising the steps of a) thermally converting, by a pyrolysis or a partial oxidation process, a feed charge containing methane into an acetylene containing effluent, and b) in situ hydrogenating, by a non-catalytic reaction, the acetylene produced in the first step into ethylene by intimately mixing the acetylene containing effluent with an ethane feed. The process according to the invention is more efficient than other synthesis schemes, while simplifying the overall process design. This process thus offers an economically attractive scheme for mass production of ethylene from natural gas, based on a well-known and proven acetylene route.

17 Claims, 2 Drawing Sheets

U.S. PATENT DOCUMENTS

Figure 1:
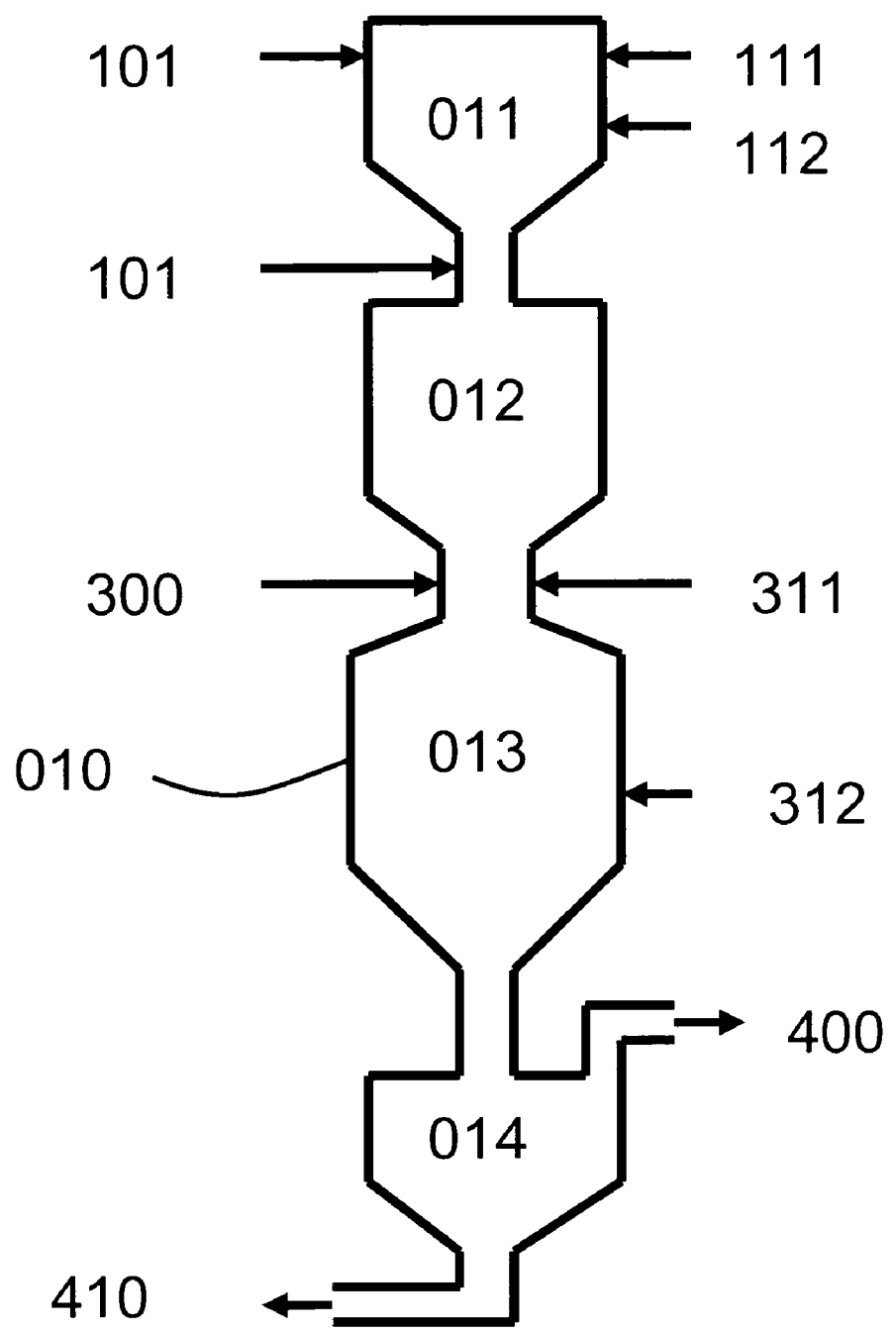

| | | | |
|---|---|---|---|
| 5,015,799 A * | 5/1991 | Walker et al. | 585/500 |
| 5,059,732 A | 10/1991 | Cosyns et al. | |
| 5,270,016 A | 12/1993 | Alagy et al. | |
| 5,585,530 A * | 12/1996 | Gough et al. | 585/257 |
| 5,789,644 A | 8/1998 | Passler et al. | |
| 5,824,834 A * | 10/1998 | Bachtler et al. | 585/540 |
| 5,847,250 A | 12/1998 | Flick et al. | |
| 7,250,449 B2 * | 7/2007 | Bullin et al. | 518/700 |
| 2005/0048658 A1 | 3/2005 | Johnson et al. | |
| 2005/0049445 A1 | 3/2005 | Johnson et al. | |
| 2005/0065391 A1 * | 3/2005 | Gattis et al. | 585/943 |
| 2005/0065392 A1 | 3/2005 | Peterson et al. | |
| 2007/0191664 A1 * | 8/2007 | Hershkowitz et al. | 585/539 |

FOREIGN PATENT DOCUMENTS

| | | |
|---|---|---|
| GB | 958046 | 5/1964 |
| JP | 58-126819 | 7/1983 |

OTHER PUBLICATIONS

Benson, et al., "Mechanisms for Some High-Temperature Gas-Phase Reactions of Ethylene, Acetylene, and Butadiene" in J. Phys. Chem., 71(6), 1735-1746 (1971).*

Rolf K. Edvinsson, et al.; Liquid-Phase Hydrogenation of Acetylene in a Monolithic Catalyst Reactor; Ind. Eng. Chem. Res. 1995, pp. 94-100 vol. 34.

* cited by examiner

PROCESS FOR THE PRODUCTION OF ETHYLENE

FIELD OF THE INVENTION

This invention relates to a process for the production of ethylene, and in particular to a process that combines traditional thermal converting of a methane-containing feed such as natural gas into acetylene, with an in situ hydrogenation step to produce ethylene.

PRIOR ART

Converting methane to acetylene by thermal pyrolysis is well a known process, such as a one step partial oxidation process described in a.o. U.S. Pat. Nos. 5,824,834 and 5,789,644. A general reactor configuration and mechanical design is described in U.S. Pat. No. 5,789,644. This design includes three major parts, one is a mixing zone with a special diffuser, the second part is a burner zone followed by a reaction zone, and the final part is a quenching zone using an aqueous coolant or heavy oil. The key innovation of this patent is the use of a perforated plate to cover the burner zone tube for special control purposes. U.S. Pat. No. 5,824,834 describes the general process scheme and some critical feed ratios, especially the carbon to oxygen ratio. This ratio is used to control the soot formation, but soot forming cannot be completely or effectively eliminated by this process. The ratio of acetylene to syngas can also be controlled by this process.

Acetylene can also be produced by means of a two stage high-temperature pyrolysis process (HTP), as described in a.o. GB 921,305 and GB 958,046. This process comprises two main reaction zones and one quenching zone. The first reaction zone, wherein preheated hydrocarbon is combusted, serves to supply the necessary heat for the second reaction zone, wherein a fresh feed of hydrocarbon to be pyrolized is injected and mixed with burnt products of the first zone. In the quenching zone water or heavy oil is used as a coolant. Also in this process some amount of carbon is produced.

The hydrogenation reaction of acetylene to ethylene over $Pd/Al_2O_3$ catalysts is also known (e.g. U.S. Pat. No. 5,847,250). Such a catalyzed reaction has been widely used to purify the ethylene produced in a steam cracker, which is contaminated with acetylene in an amount of typically less than 1.5%. This traditional hydrogenation scheme is not economical for mass production of ethylene from acetylene. Another drawback of using the traditional hydrogenation scheme for this purpose is the oligomerization of acetylene into heavy hydrocarbons, which are the precursors of green oil and coke fragments. Because of these undesirable side reactions, the catalyst is deactivated very fast and needs regeneration steps. In addition, some ethylene may be lost due to consecutive deep hydrogenation reactions. Furthermore, because of the high exothermic heat of reaction, the reactor temperature may run away, thus causing a decline of catalyst selectivity. It thus appears that vapor-phase hydrogenation of acetylene is a process that is difficult to control, especially with high acetylene concentration.

On the other hand, the hydrogenation temperature may be controllable in a liquid-phase reactor, through which an adequate volume of liquid solvent is re-circulated continuously to maintain a steady temperature so as to reduce the deactivation rate of a catalyst, while the acetylene is mainly dissolved in the solvent. However, the type of solvent can affect the extent of hydrogenation as illustrated in U.S. Pat. No. 4,128,595. For this practice, the hydrogenation reaction has been carried out at 116-193° C. in the presence of $Pd/Al_2O_3$ catalyst with an inert paraffinic hydrocarbon solvent. Acetylene conversion was maintained at 99% with 84% selectivity for 9 days. However, if DMF solvent is used instead, the acetylene conversion dropped from 100% to 50% in about 17 hours with 75% selectivity.

Similar liquid-phase hydrogenation of acetylene has been described in U.S. Pat. No. 5,059,732, wherein gasoline was used as a liquid medium. This method improved the catalyst life, but it induced the formation of heavy hydrocarbons through the oligomerization of acetylene.

Publications US 2005/0048658 A1 and US 2005/0049445 A1 disclose a method of acetylene hydrogenation by using NMP as liquid solvent, and by passing over a Pd-based catalyst. In these publications the reported concentration of acetylene dissolved in the solvent is about 4.2%. Based on such information, it can be concluded that the reactor size would be uneconomically large for mass production of ethylene. This method cannot effectively eliminate oligomerization of acetylene either. Although the catalyst was stable for about 6 days (140 hours), it still needed a regeneration step to sustain its activity. US 2005/0065392 A1 discloses a pyrolysis process for acetylene production followed by a traditional liquid-phase hydrogenation scheme downstream. The scheme to be implemented complicates the process design in addition to the limited specific production rate due to the acetylene solubility in the solvent.

Deactivation of Pd-containing catalysts by green oil during acetylene hydrogenation was also described in scientific literature (R. K. Edvinsson, A. M. Holmgren and S. Irandoust, Ind. Eng. Chem. Res. 1995, 34, 94-100). These authors suggested that a special type of monolith reactor can be used for the gas/liquid/solid acetylene hydrogenation reaction. In that work, acetylene hydrogenation was carried out in the presence of $Pd/\alpha-Al_2O_3$ on the surface of monolithic support in the liquid phase at 40° C. and 20 atm pressure with using 3% $C_2H_2$+28% $C_2H_4$+6% to 11% $H_2$+$N_2$ (balance) mixture. The selectivity to ethylene dropped significantly with the increase of $C_2H_2$ conversion. At 90% of $C_2H_2$ conversion, the selectivity of $C_2H_2$ to ethylene was found to be 60%. Nevertheless, the catalyst was not stable in continuous experiments. After 50 hours, the selectivity to ethylene started to decrease. It was also indicated that the influence of the presence of CO in the gas feed mixture was detrimental to the catalyst rate of hydrogenation; at 2400 ppm of CO the hydrogenation reaction stopped completely. The reduction of hydrogenation rate was attributed to CO blocking some of the hydrogen adsorption sites. Clearly it is a must to include a CO purification step in a traditional catalytic hydrogenation process.

A similar concept of catalytic hydrogen transfer was mentioned and practiced in prior art at quiet different reaction conditions (U.S. Pat. Nos. 3,267,170 and 3,321,545). However, the performance pertaining to such a reaction is still constrained by catalyst activity and selectivity. This also requires a separate hydrogen transfer reactor downstream, and requires a prior gas-purification step.

Publication JP58-126819A discloses a non-catalytic process of acetylene conversion to ethylene. The product obtained by pyrolysis of ethane and naphtha is first separated in a C2 fraction and other fractions (C1, C3, C4 etc.). The C2 fraction (acetylene, ethylene, and ethane) is then introduced into an acetylene separation zone, from where pure acetylene is recovered. The pure acetylene obtained is subsequently diluted with ethane in a separate process unit and subjected to pyrolysis. A maximum of 70.6% acetylene conversion is provided. This process is rather complicated, as ethylene is obtained from acetylene in a sequence of purification steps before reduction with ethane.

SUMMARY OF THE INVENTION

The known processes for producing ethylene from a methane-containing feed show several disadvantages, like catalyst deactivation, deep hydrogenation, green oil or carbon formation, temperature runaway problems, or a low production rate per unit reactor volume. There is thus a need in industry for an improved process, especially allowing more efficient and stable hydrogenation of acetylene into ethylene.

The present invention provides such an improved process for the production of ethylene, which process comprises the steps of
- thermally converting, by a pyrolysis or a partial oxidation process, a feed charge containing methane into an acetylene containing effluent, and
- in situ hydrogenating, by a non-catalytic reaction, the acetylene produced in the first step into ethylene by intimately mixing the acetylene containing effluent with an ethane feed.

The process according to the invention proved to be more efficient than other synthesis schemes, while simplifying the overall process design. This process thus offers an economically attractive scheme for mass production of ethylene from natural gas, based on a well-known and proven acetylene route. In this new process scheme proven methods for making acetylene from natural gas by a thermal reaction route can be used to produce the acetylene as an intermediate product, which acetylene is immediately hydrogenated by a non-catalytic in-situ hydrogenation reaction. Said hydrogenation reaction is considered to be based on a so-called hydrogen transfer mechanism. Such non-catalytic hydrogenation step is convenient for design and operation of a high temperature reactor. In this way both pyrolysis and hydrogenation can be performed in a single process unit, or integrated reactor. The ethane added during the hydrogenation step is thought to function as a template-like reagent to initiate and promote the desired reactions to form ethylene.

In U.S. Pat. No. 5,270,016 also a process for thermal conversion of methane to hydrocarbons of higher molar mass, like acetylene and ethylene, is disclosed. In this process the products obtained after thermal conversion are quenched by bringing them into direct contact with a cooling fluid, which cooling fluid can be a liquefied petroleum gas, propane, a hydrocarbon oil or water. Propane is indicated to be the preferred compound for cooling. U.S. Pat. No. 4,726,913 relates to a process for making synthesis gas and hydrocarbons, wherein methane may be used as feed and acetylene, ethylene and synthesis gas are products obtained. After thermal conversion, the reaction products may be quenched with liquid saturated hydrocarbons such as propane, butane or gasoline. These publications, however, do not disclose or suggest to mix the acetylene-containing effluent with ethane to optimize yields of ethylene and acetylene in a non-catalytic hydrogenation step.

Various feed compositions can be used as the methane containing feed charge, as well as different sources of methane. Preferably, natural gas as used as methane source for the methane-containing feed. The feed may further contain pre-mixed and preheated components, such as (in addition to methane) oxygen, air, hydrogen, carbon monoxide, carbon dioxide, etc.

In a preferred embodiment of the invention, the pyrolysis process is a two-stage process, more preferably a high temperature pyrolysis process (HTP). In such HTP process, preferably a methane containing feed and oxygen are preheated to a temperature of from about 550° C. to 650° C., and are fed in stoichiometric ratio or with oxygen slightly below stoichiometric ratio and reacted in a combustion zone (stage 1) to form to gases, at a temperature of from about 900° C. to 2000° C. and a pressure in the range of from 0.5 to 5 atmospheres (0.05-0.5 MPa), and wherein the hot combustion gas is then passed on to a pyrolysis zone to which additional methane is introduced (stage 2) to form acetylene. The pyrolysis zone is maintained at a temperature of about 1300° C. to 1600° C., the contact time in this zone is from about 3 to 30 milliseconds and the pressure is maintained from 0.5 to 5 atmospheres (0.05-0.5 MPa).

More preferably, in the pyrolysis zone (stage 2), the contact time is from 5 to 10 milliseconds and the pressure is maintained at about 2 atmospheres.

In a preferred embodiment, the methane containing feed is fed into the pyrolysis zone (stage 2) after preheating to about 600° C.

In another aspect of the invention, a partial oxidation process comprises preheating the methane containing feed and oxygen to a temperature of from 600° C. to 700° C., wherein the oxygen to methane feed ratio is sub-stoichiometric; for example from 0.5 to 0.7, preferably about 0.62; and wherein the temperature in the pyrolysis zone is from 1500° C. to 1600° C.

In a further preferred embodiment, the acetylene containing mixture is cooled by partial quenching using a coolant, before the in situ hydrogenation reaction takes place.

Suitable coolants are known to the skilled person, the coolant is preferably selected from the group consisting of water, heavy hydrocarbons, natural gas, methanol and mixtures thereof.

Preferably, the temperature of the acetylene containing gases after partially quenching is between 800° C. and 950° C., more preferably between 800° C. and 910° C.

The reduction in temperature in the partial quench step is preferably achieved by spray injection of the coolant into the acetylene containing gases.

In the process according to the invention, the in situ hydrogenation is performed by intimately mixing the acetylene containing effluent from the thermal pyrolysis or partial oxidation zone with an ethane feed to enhance the conversion of acetylene into ethylene.

In a preferred embodiment, the ethane feed rate and its temperature, together with the rate of coolant addition, are adjusted to keep the hydrogenation temperature in the range from 800° C. to 950° C., more preferably from 800° C. to 910° C.

The ethane feed may be added separately to the hydrogenation zone, or pre-mixed with the coolant.

The amount of ethane to be added to the reactor is not very critical. Preferably, the ethane to acetylene molar ratio ranges from 4:1 to 0.2:1, more preferably from 1:1 to 0.25:1, to optimize ethylene yield.

Preferably, the contact time in the hydrogenation zone is from 0.01 to 1.0 seconds, more preferably from 0.05 to 0.8 seconds, and the pressure is from 0.5 to 5 atmospheres (0.05-0.5 MPa).

In a preferred embodiment, the hydrogenation zone is not limited to a single partial quench with coolant, but may be extended to comprise multiple partial quench zones for better temperature control, and to prevent temperature runaway resulting from the exothermic heat of hydrogenation reactions.

A final quench may be conducted for stabilizing the product gases containing ethylene, to bring the temperature of said gases to a temperature of from about 90° C. to 150° C.

The coolant used may be water, heavy oil or natural gas.

In a further embodiment of the process of the invention, the residual acetylene remaining in the final quenched product gas, further containing a.o. unconverted ethane, is separated downstream, and recycled back together with make-up ethane feed to the in situ hydrogenation zone.

In another preferred embodiment, unconverted methane is separated from the final quenched product downstream, and is recycled back to the primary feed charge containing methane), or used as fuel gas.

Moreover, it is also preferred that $C_3$ and higher unsaturated and aromatic compounds contained in the final effluent gases are separated downstream.

The effluent from the thermal partial oxidation/pyrolysis processes typically contain 10-20% acetylene, 5-30% $H_2$, 30-40% $H_2O$ and 9-40% CO, and can be fed to a secondary hydrogenation reaction zone without any further treatment. To have the best process performance such reactor will operate with a contact time of 0.05 to 1.0 seconds, preferably from 0.14 to 0.6 second, at a temperature of 800° C. to 1000° C., preferably between 860° C. and 910° C., and at a pressure of 0.5 to 5 atmospheres. This can be achieved by using a proper reactor configuration and partial quenching with a coolant and ethane. The preferred molar ratio of ethane to acetylene is between 4:1 and 0.2:1, most preferred between 1:1 and 0.25:1. With the process according to the invention conversions of acetylene to ethylene of 85-92% can be achieved. The ethylene selectivity from combined ethane and acetylene is 60-65%. Most acetylene which is not converted to ethylene is mainly converted back to saturated alkanes and higher alkenes such as methane, ethane, propylene and butylenes, instead of being decomposed to coke or forming green oil, which is an additional advantage of the process of the invention. Based on the commercially established method to produce acetylene (i.e. partial oxidation or pyrolysis), the overall ethylene yield may range between 17-45% related to methane feed.

The process according to the invention results in an outlet mixture, wherein the acetylene concentration is as low as 0.8-1.2 mol %; which means it can be safely recycled back to the hydrogenation zone with the ethane feed, thus simplifying overall plant operation.

The process of the invention thus shows significant advantages over the prior art, because it does not suffer from temperature runaway, or from catalyst deactivation resulting from green oil formation or catalyst poisoning by a high CO concentration. This significantly simplifies downstream processing units, e.g. omission of units for gas pretreatment units for CO removal; and thus reduces operating and capital cost of an ethylene plant. In addition, carbon formation resulting from thermal cracking of higher hydrocarbon species in the outlet gases can be substantially suppressed by the present in situ hydrogenation step.

SHORT DESCRIPTION OF THE DRAWINGS

Figure 2:
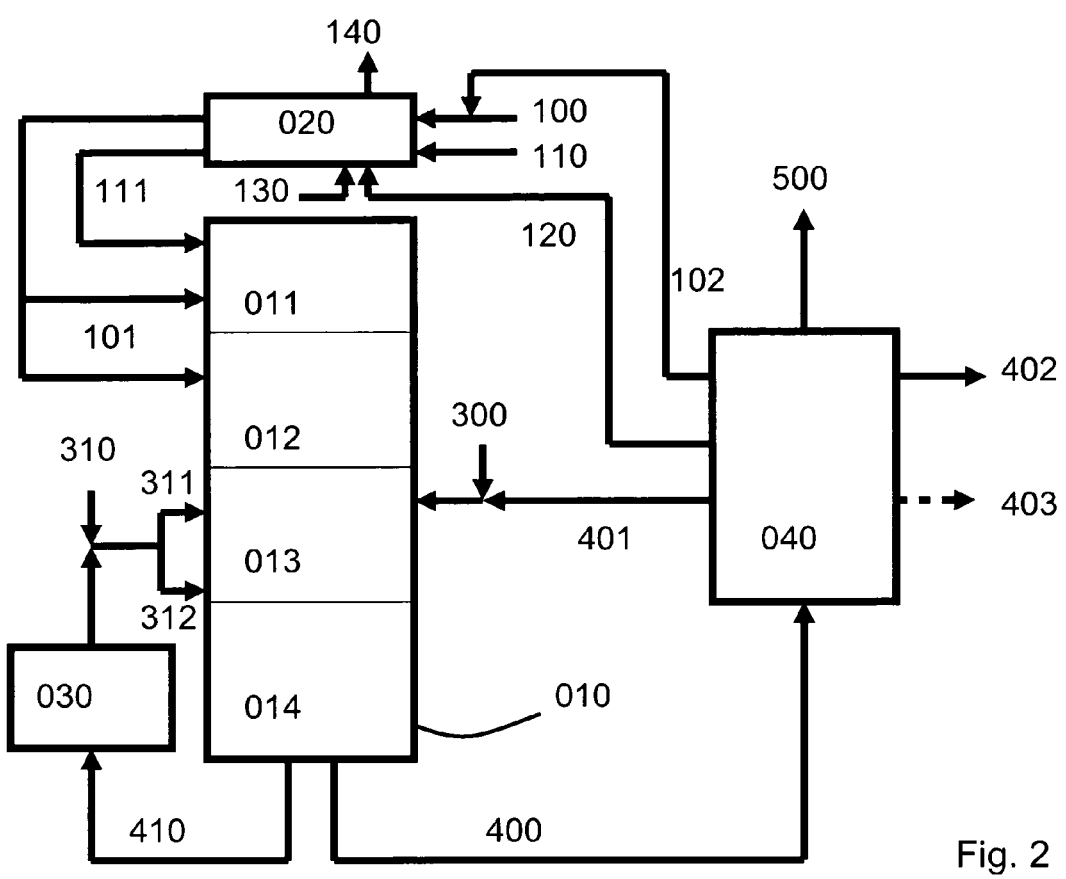

FIG. 1 schematically shows an integrated reactor suitable for performing the process according to the invention including thermal pyrolysis and in-situ hydrogenation steps; and FIG. 2 shows a schematic flow diagram of the inventive process for making ethylene from natural gas. Identical numbers in FIG. 1 and FIG. 2 have the same meaning.

PREFERRED EMBODIMENTS

As described above, the combined thermal pyrolysis and in-situ hydrogenation process of the invention can be operated as a compact single unit operation to produce ethylene from natural gas with an economically acceptable yield, in a reactor (010) as schematically shown in FIG. 1. The integrated reactor (010) comprises four zones (011, 012, 013 and 014). The first zone (011) is referred to as the (stoichiometric) combustion zone; the second zone (012) as (thermal) pyrolysis zone; in zone 3 (013) the in situ hydrogenation reaction takes place; and in zone 4 (014) gases and liquids are separated. Pre-heated methane-containing feed (101) is entered into the reactor together with oxygen (111) and optionally other components (112), like for example steam. Ethane (300) is fed to the next zone (013), as well as a cooling medium in two steps (311, 312). Liquid cooling medium (410) from the separation zone (014) is returned for quenching, reaction products (400) are further treated in product recovery steps.

In a preferred embodiment of the invention, the process includes the so-called Hoechst two-stage pyrolysis scheme to result in a high conversion of methane per pass. The general process scheme is shown in FIG. 2. Methane (100) obtained from natural gas is combined with unconverted methane recovered from reactor effluent (102) and is preheated to about 600° C. in feed pre-heater (020). An oxygen stream, e.g. oxygen from a plant (110) and air (130), is also preheated to about 600° C. before feeding to the reactor (111). The reactor effluent containing CO and hydrogen (120) will be used as a fuel gas for feed preheating and steam generation. Flue gas leaving the preheater is indicated as (140). The preheated methane (101) is split into two streams, of which one is fed to the mixing and combustion zone at a stoichiometric ratio with oxygen feed for complete combustion to supply the necessary heat for the endothermic reaction in the pyrolysis zone. The other methane stream (101) is fed to the pyrolysis zone (012) directly.

In the combustion zone the reactor wall can be protected from high temperature by a steam curtain if necessary.

In the combustion zone (011) the temperature typically ranges between 900° C.-2000° C. In the pyrolysis section the preheated methane is quickly mixed with effluents from the combustion zone at 1300° C.-1600° C. to form acetylene. The desired residence time in the pyrolysis section is controlled in the range of 3 and 30 milliseconds, preferably between 5 and 10 milliseconds. The pressure is set in the range of about 0.5-5 atmosphere (about 0.05-0.5 MPa) and preferably about 0.5-2 atmospheres. Up to this point the traditional two stage pyrolysis is implemented.

In the preferred embodiment of the process according to the invention, the pyrolysis products from the pyrolysis zone are first partially quenched to the desired hydrogenation reaction temperature, which is typically in the range from 800 to 950° C., preferably from 800 to 910° C. Such quenching can be effected by adding a suitable cooling medium (310, 311), optionally mixed with the ethane component (300). Said last component can also be added separately. The cooling medium is preferably water, natural gas or methanol, but oil can also be used. By adding ethane to the partially quenched pyrolis products most of the acetylene is converted to ethylene by hydrogen transfer. This particular zone is referred to in this disclosure as in-situ hydrogenation zone (013). The required contact time may vary between 0.05 and 1.0 seconds, preferably from 0.14 to 0.6 seconds, and the pressure is set between 0.05 and 0.5 MPa. The ethane to acetylene ratio can vary from 4:1 to 0.2:1. After hydrogenation is complete, the reaction gas is further quenched with a coolant (312) down to 200° C.-90° C. for product recovery. A multi-step quench, for example a two-step quench, is preferred for this in-situ hydrogenation operation.

The unconverted acetylene and unconverted alkane are separated (400; 040) and recycled back together to the in-situ hydrogenation zone (401), preferably mixed with fresh feed of ethenol (300) and coolant (310). The remainder gas mixture (120), mainly hydrogen and CO mixed with some $CO_2$ is used as fuel gas. By using this process scheme there is enough fuel gas to preheat the feed streams to the required temperatures.

In addition to by-products like propylene, butylenes, benzene, etc. (402) and other unspecified heavies and carbon (403), the main product ethylene (500) is obtained from the product recovery unit (040).

In another embodiment of the process according to the invention, a BASF-type partial oxidation reactor can be used in a similar way as described above to make acetylene, which is then in-situ hydrogenated in a similar hydrogenation zone to produce ethylene.

Ethylene mass production from natural gas can therefore be economically realized by using the compact process design according to the invention.

EXAMPLES

Detailed information on the pyrolysis and partial oxidation step as applied is available in prior art documents, for example in references mentioned above. All experiments were conducted in a 4 ml ID quartz reactor, at atmospheric pressure (unless indicated otherwise) Typical results are as follows:

Example 1

These experiments show the main reaction between acetylene and an alkane feed such as ethane at a reaction temperature between 880° C. and 890° C. The conversion of acetylene was higher than 90%, while the conversion of ethane was higher than 75%. Additional hydrogen used to hydrogenate the acetylene evidently came from the free hydrogen available in the feed. This is quite different from the experiments in Example 2, wherein no ethane was added to the feed.

The flow rate of the feed was controlled to have a constant time. For a typical case when ethane was added to a pyrolysis product gas containing syngas, acetylene and water a feed comprising 8.6% $C_2H_2$, 4.4% $C_2H_6$, 5.5% $N_2$, 13% CO, 68.5% $H_2$ and water (at 0.06 cc/min) was tested. The observed results from the hydrogen transfer reaction are shown in Table 1.

TABLE 1

| Temperature (° C.) | 880 | 890 |
|---|---|---|
| $C_2H_2/C_2H_6$ mole ratio | 1.95 | 1.95 |
| $C_2H_2$ conversion (%) | 90.0 | 92.2 |
| $C_2H_6$ conversion (%) | 75.3 | 77.2 |
| Total $C_2H_4$ selectivity (%) | 63.5 | 60.7 |
| Outlet $C_2H_2$ concentration (%) | 1.31 | 1.16 |
| Outlet $C_2H_6$ concentration (%) | 1.12 | 0.95 |
| Outlet $C_2H_4$ concentration (%) | 7.60 | 7.90 |
| Contact time (s) | 0.43 | 0.43 |

Additionally it can be seen that a high concentration of CO has no effect on acetylene hydrogenation, in contrast to a process including catalytic acetylene hydrogenation on Pd-based catalysts. In general, not more than 500 ppm of CO can be tolerated in the feed to a catalytic hydrogenation reactor.

Example 2

To demonstrate the effect of ethane addition to the in-situ hydrogenation reaction a separate experiment was conducted, wherein acetylene hydrogenation in absence of alkane feed is compared to the effect of switching the feed with ethane present in the same experiment. A contact time of 0.44 seconds was maintained. As can be seen with ethane present in the feed the formation of ethylene in column one is more than three times higher than its concentration with no ethane in the feed.

Table 2 also shows the full outlet composition: some higher hydrocarbons were formed as byproducts of the hydrogenation step in the outlet gas. Only little traceable carbon is observed in the particular hydrogenation step after many days on stream.

TABLE 2

| Temperature (° C.) | $C_2H_4$ | $C_2H_2$ | $C_2H_6$ | $N_2$ | $H_2$ | $C_3H_6$ | $C_4H_8$ | $C_6H_6$ | $CH_4$ |
|---|---|---|---|---|---|---|---|---|---|
| With ethane | | | | | | | | | |
| Feed | — | — | 8.8 | 17.2 | 36.0 | 37.2 | | | |
| Run 858 | 12.75 | 2.13 | 3.47 | 37.1 | 41.4 | 0.07 | 0.31 | 0.47 | 2.19 |
| Without ethane | | | | | | | | | |
| Feed | — | — | 13.7 | — | 43.9 | 42.5 | | | |
| Run 855 | 3.97 | 4.53 | 0.30 | 48.0 | 41.5 | — | 0.20 | 0.43 | 0.86 |

Example 3

This series of experiments were carried out at different temperatures, with contact time for the hydrogenation reaction kept constant. A gas mixture of 8.79 mol % $C_2H_2$, 4 mol % $N_2$, 83.9 mol % $H_2$, and 3.05 mol % $C_2H_6$ was used with a flow rate 107 cc/min and with water flow 0.06 cc/min. The pressure in the reactor was atmospheric.

From the results shown in Table 3 it can be concluded that conditions can be optimized, to maximize the ethylene concentration in the outlet.

The main reaction product was ethylene, small amounts of $CH_4$, $C_3H_6$, $C_4H_8$ and benzene were found as byproducts. Some byproducts such as alkenes and benzene are considered recoverable valuable byproducts.

TABLE 3

| Temperature (° C.) | 855 | 870 | 901 | 915 | 932 |
|---|---|---|---|---|---|
| $C_2H_6/C_2H_2$, mole ratio | 0.34 | 0.34 | 0.34 | 0.34 | 0.34 |
| $C_2H_2$ conversion (%) | 79.3 | 84.1 | 88.8 | 89.8 | 92.9 |
| $C_2H_6$ conversion (%) | 56.1 | 65.0 | 59.9 | 66.7 | 64.6 |
| Total $C_2H_4$ selectivity (%) | 59.6 | 54.5 | 59.8 | 57.1 | 52.0 |
| Outlet $C_2H_2$ concentration (%) | 2.1 | 1.67 | 1.14 | 1.05 | 0.74 |
| Outlet $C_2H_6$ concentration (%) | 1.54 | 1.24 | 1.42 | 1.19 | 1.29 |
| Outlet $C_2H_4$ concentration (%) | 6.0 | 6.12 | 6.71 | 6.67 | 6.33 |
| Contact time (s) | 0.44 | 0.44 | 0.43 | 0.43 | 0.42 |

Example 4

In this experiment the effect of contact time on hydrogenation was evaluated at a constant reaction temperature of 896° C., the results are shown in Table 4. Feed gas composition used was 12.88% $C_2H_2$, 1.79% $C_2H_6$, 5.85% $N_2$, and 79.4% $H_2$ with the addition of 0.06 ml/min $H_2O$. The results reveal that the ethylene concentration can be changed by varying contact time.

TABLE 4

| Contact time (s) | 0.43 | 0.28 | 0.14 |
|---|---|---|---|
| $C_2H_2$ conversion (%) | 93.0 | 68.0 | 53.0 |
| $C_2H_6$ conversion (%) | 16.0 | 60.0 | 72.2 |
| Total $C_2H_4$ selectivity (%) | 46.4 | 56.6 | 57.9 |
| Outlet $C_2H_2$ concentration (%) | 1.06 | 4.41 | 6.15 |
| Outlet $C_2H_6$ concentration (%) | 1.18 | 0.54 | 0.52 |
| Outlet $C_2H_4$ concentration (%) | 6.37 | 5.75 | 4.70 |

Example 5

Besides ethane, higher alkanes were also tested such as propane. The result at different temperatures is shown Table 5 and indicates that propane is not as effective as ethane. The feed composition was 12.03% $C_2H_2$, 14.57% $C_3H_8$, 36.7% $N_2$ and 36.65% $H_2$ with water 0.06 cc/min.

TABLE 5

| Temperature (° C.) | 683 | 750 | 831 | 841 |
|---|---|---|---|---|
| $C_3H_8/C_2H_2$ (mole ratio) | 1.2 | 1.2 | 1.2 | 1.2 |
| $C_2H_2$ conversion (%) | 4.56 | 22.1 | 67.9 | 88.5 |
| $C_3H_8$ conversion (%) | 25.4 | 27.6 | 45.8 | 55.1 |
| Total $C_2H_4$ selectivity (%) | 52.3 | 50.1 | 56.6 | 56.5 |
| Outlet $C_2H_2$ concentration (%) | 9.22 | 8.78 | 6.41 | 5.23 |
| Outlet $C_3H_8$ concentration (%) | 14.3 | 11.45 | 4.59 | 1.63 |
| Outlet $C_2H_4$ concentration (%) | 1.99 | 3.3 | 8.56 | 10.97 |
| Contact time (s) | 0.52 | 0.49 | 0.45 | 0.45 |

The invention claimed is:

1. A process for the production of ethylene, comprising the steps of
   (a) thermally converting, by a pyrolysis or a partial oxidation process, a feed charge containing methane into an acetylene containing effluent, and
   (b) in situ hydrogenating, by a non-catalytic reaction, the acetylene produced in the first step into ethylene by intimately mixing the acetylene containing effluent with an ethane feed.

2. The process according to claim 1, wherein the pyrolysis process is a two-stage process.

3. The process according to claim 2, wherein the pyrolysis process is a high temperature pyrolysis process.

4. The process according to claim 1, wherein the pyrolysis or partial oxidation process comprises preheating the feed containing methane and oxygen to a temperature of from 600° C. to 700° C., wherein the oxygen to methane molar feed ratio is from 0.5 to 0.7, and wherein the temperature in the pyrolysis process is from 1500° C. to 1600° C.

5. The process according to claim 4, wherein the oxygen to methane molar feed ratio is about 0.62.

6. The process according claim 1, wherein the acetylene containing effluent is partially quenched using a coolant, before the in situ hydrogenation reaction takes place.

7. The process according to claim 6, wherein the coolant is selected from the group consisting of water, heavy hydrocarbons, natural gas, methanol and mixtures thereof.

8. The process according to claim 6, wherein the temperature of the acetylene containing effluent after partially quenching is between 800° C. and 950° C.

9. The process according to claim 6, wherein rate and temperature of the ethane feed, and of coolant addition are adjusted to keep the hydrogenation temperature in the range from 800° C. to 950° C.

10. The process according to claim 1, wherein the ethane feed is added separately to the in situ hydrogenation reaction.

11. The process according to claim 1, wherein the ethane to acetylene molar ratio ranges from 4:1 to 0.2:1.

12. The process according to claim 11, wherein the ethane to acetylene molar ratio ranges from 1:1 to 0.25:1.

13. The process according to claim 1, wherein contact time in the in situ hydrogenation reaction is from 0.01 to 1.0 seconds and the pressure is from 0.05 to 0.5 MPa.

14. The process according to claim 6, wherein the in situ hydrogenation reaction comprises multiple partial quench zones.

15. The process according to claim 1, wherein a final quench is conducted to bring the temperature of product gases containing ethylene to a temperature of from 90° C. to 150° C.

16. The process according to claim 15, wherein residual acetylene and unconverted ethane in the product gas is separated downstream and recycled back, together with a make-up ethane feed, to the in situ hydrogenation reaction.

17. The process according to claim 6, wherein rate and temperature of the ethane feed, and of coolant addition are adjusted to keep the hydrogenation temperature in the range from 800° C. to 910° C.

\* \* \* \* \*